US012779193B2

(12) United States Patent
Hitzeroth et al.

(10) Patent No.: US 12,779,193 B2
(45) Date of Patent: Nov. 3, 2026

(54) COMPOUND VALVE SYSTEM FOR INTRACARDIAC TOOLS

(71) Applicant: Biosense Webster (Israel) Ltd., Yokneam (IL)

(72) Inventors: Matthew W. Hitzeroth, Irwindale, CA (US); David Maher, Irvine, CA (US); Raymond Yue-Sing Tang, Irvine, CA (US); Mark Stanley, Irvine, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 1070 days.

(21) Appl. No.: 17/957,453

(22) Filed: Sep. 30, 2022

(65) Prior Publication Data

US 2023/0137558 A1 May 4, 2023

Related U.S. Application Data

(60) Provisional application No. 63/272,722, filed on Oct. 28, 2021.

(51) Int. Cl.
*A61M 39/06* (2006.01)
*A61M 25/06* (2006.01)

(52) U.S. Cl.
CPC .... *A61M 39/0613* (2013.01); *A61M 25/0662* (2013.01); *A61M 2025/0681* (2013.01); *A61M 2039/062* (2013.01); *A61M 2039/0673* (2013.01); *A61M 2039/0686* (2013.01)

(58) Field of Classification Search
CPC .............. A61M 39/06; A61M 39/0613; A61M 39/0693; A61M 2039/062;
(Continued)

(56) References Cited

U.S. PATENT DOCUMENTS 4,331,147 A * 5/1982 Armstrong .............. A61M 1/66 604/362
5,180,365 A * 1/1993 Ensminger ........ A61M 39/0208 604/288.03
(Continued)

FOREIGN PATENT DOCUMENTS

WO 2001070308 A1 9/2001

OTHER PUBLICATIONS

Extended European Search Reported and Opinion dated Mar. 3, 2023, from corresponding European Application No. 22203991.9.
(Continued)

*Primary Examiner* — Kami A Bosworth

(57) ABSTRACT

Disclosed herein is a system for treatment including a compound valve system that can be integral to, or attached to a sheath introducer. The compound valve system includes a secondary valve that can be positioned in a proximal direction from a primary valve of the sheath introducer. The secondary valve can move longitudinally in response to a pressure differential. The compound valve system can include an aspiration port between the primary valve and secondary valve. The secondary valve can be integral to a secondary valve accessory device that can be assembled onto a catheter shaft of an intralumenal treatment device, and the secondary valve accessory device can further function as an introducer tool for the intralumenal treatment device.

12 Claims, 11 Drawing Sheets

(58) Field of Classification Search
CPC .. A61M 2039/0626; A61M 2039/0633; A61M 2039/064; A61M 2039/0646; A61M 2039/0653; A61M 2039/0666; A61M 2039/0686; A61M 2039/2406; A61M 39/0606; A61M 39/068; A61M 39/24; A61M 2039/0673; A61M 2039/2493; A61B 17/3498
See application file for complete search history.

(56) References Cited

U.S. PATENT DOCUMENTS

| | | | | |
|---|---|---|---|---|
| 5,197,955 | A * | 3/1993 | Stephens ............... | A61M 39/06<br>604/167.01 |
| 5,324,271 | A | 6/1994 | Abiuso et al. | |
| 5,492,304 | A * | 2/1996 | Smith ................ | A61B 17/3462<br>251/342 |
| 5,657,963 | A * | 8/1997 | Hinchliffe ............. | A61M 39/06<br>604/167.01 |
| 10,046,141 | B2 | 8/2018 | Schultz | |
| 2010/0193516 | A1 * | 8/2010 | LaBean ................ | B65D 51/002<br>220/229 |
| 2012/0065612 | A1 * | 3/2012 | Stout ................. | A61M 25/0693<br>604/168.01 |
| 2019/0076640 | A1 | 3/2019 | Bhatnagar et al. | |

OTHER PUBLICATIONS

Exam Report dated Jul. 23, 2025, from corresponding European Application No. 22203991.9.

* cited by examiner

COMPOUND VALVE SYSTEM FOR INTRACARDIAC TOOLS

CROSS REFERENCE TO RELATED APPLICATION

This application claims the benefit of priority to prior filed U.S. Provisional Patent Application No. 63/272,722 filed on Oct. 28, 2021, which is hereby incorporated by reference as set forth in full herein.

FIELD

The present invention relates to valves for catheter delivery, and in particular hemostasis valves for a sheath introducer.

BACKGROUND

A “sheath” or “sheath introducer” includes a tube placed in an artery or vein of a patient during a medical procedure that, when positioned for treatment, has a distal end within the artery or vein and a proximal end outside of the patient. A hemostasis valve at the proximal end of the sheath inhibits blood from exiting the sheath and allows longer sheaths and/or catheters to be inserted through the sheath into the artery or vein.

A problem with some current sheath introducers for catheter delivery is that movement of devices through the sheath can result in a pressure differential between an inner lumen of the sheath and the ambient environment which can potentially allow for air entrainment and/or leakage through the seal of the sheath.

SUMMARY

The present invention relates to valves for catheter delivery, and in particular hemostasis valves for a sheath introducer.

An example catheter sheath assembly can include an elongated shaft, a primary hemostatic valve assembly, and a secondary hemostatic valve assembly. The elongated shaft can include a distal end, a proximal end, and a lumen extending along a longitudinal axis and providing a passageway into the proximal end of the shaft and out of the distal end of the shaft. The primary hemostatic valve assembly can fluidically seal to the proximal end of the elongated shaft and include a primary seal. The secondary hemostatic valve assembly can include a secondary seal disposed in a proximal direction in relation to the primary seal such that the primary hemostatic valve assembly and the secondary hemostatic valve assembly define an intermediate chamber disposed at least in part between the primary seal and the secondary seal.

The secondary seal can be movable in relation to the primary seal to thereby change an internal volume of the intermediate chamber. The secondary seal can be configured to slide parallel to the longitudinal axis and within a housing portion of the secondary hemostatic valve assembly. The housing portion can be fixed in relation to the primary seal. The change in volume can be equal to an interior cross-sectional area of the intermediate chamber orthogonal to the longitudinal axis multiplied by a change in longitudinal position of the secondary seal. The secondary seal can be configured to move in response to a pressure differential between the intermediate chamber and an external environment. The internal volume of the intermediate chamber being configured to change in response to a difference in pressure between the intermediate chamber and an external environment.

The secondary hemostatic valve assembly can further include one or more springs configured to change in length to thereby move the secondary valve opening in relation to the primary valve opening. The change in volume can be based at least in part on stiffness of the one or more springs. The one or more springs can be configured to compress to increase the volume of the intermediate chamber.

The primary seal can include a primary valve opening aligned to the longitudinal axis. The secondary seal can include a secondary valve opening aligned to the longitudinal axis.

The intermediate chamber can be fluidically sealed from an external environment by the secondary seal and can be sealed from the lumen of the elongated shaft by the primary seal.

The intermediate chamber can be shaped by a tubular housing portion extending between the secondary seal and the primary seal.

The catheter sheath assembly can further include a handle joining the elongated shaft to the primary hemostatic valve assembly. The handle can be configured to be manipulated to reshape the elongated shaft. The secondary hemostatic valve assembly can include latch extensions configured to slide over a proximal end of the handle and latch to the proximal end of the handle to thereby create the intermediate chamber. Alternatively, the secondary hemostatic valve assembly can be integral to the handle.

The primary valve opening can be expandable to a larger diameter than the secondary valve opening.

The catheter sheath assembly can further include an aspiration port in fluidic communication with the fluidically sealed chamber.

The catheter sheath assembly can further include an interior housing including a funnel opening have a wide proximal end positioned in a distal direction from the secondary seal and a narrow distal end positioned in a proximal direction from the primary seal.

The interior housing can be configured to urge an intraluminal device being inserted into the proximal end of the catheter sheath assembly toward the longitudinal axis and the primary valve opening.

An example assembly can include a secondary valve accessory device and a catheter. The secondary valve accessory device can include a secondary seal, a tubular inner housing extending distally from the secondary seal, and an outer housing structurally supporting the secondary seal and the tubular inner housing. The catheter can include an elongated shaft and an end effector. The elongated shaft can define a longitudinal axis and extend through the secondary seal. The end effector can be positioned within the tubular inner housing.

The outer housing can further include a mating feature configured to engage a proximal end of a sheath introducer. The mating feature can include a latch extension. Additionally, or alternatively, the mating feature can include threads.

The tubular inner housing can include a distal end configured to seal to a proximal end of a primary hemostasis valve of a sheath introducer so that an intermediate chamber is bounded by the tubular inner housing, the secondary seal, and a primary seal of the primary hemostasis valve.

The secondary valve accessory device can include an O-ring disposed around an outer surface of the tubular inner housing.

The tubular inner housing can include a tapered portion having a wider diameter approximate the secondary seal and tapering to a narrow diameter distally from the secondary seal.

The secondary seal can include a secondary valve opening sized to allow the elongated shaft of the catheter to slide longitudinally therethrough and sized to inhibit the end effector of the catheter to slide longitudinally therethrough.

The secondary seal can be configured to translate proximally in relation to the tubular inner housing and outer housing in response to a force applied in a proximal direction to the secondary seal.

The secondary valve accessory device can further include a spring providing a spring force between the secondary seal and the outer housing.

The assembly can further include a sheath introducer including a primary hemostatic valve assembly. The primary hemostatic valve assembly can include a primary seal. The sheath introducer can be attached to the secondary valve accessory device such that the secondary seal is positioned in a distal direction in relation to the primary seal and an intermediate chamber is bounded at least in part by the secondary seal, the primary seal, and the tubular inner housing.

An example method of treatment can include one or more of the following steps presented in no particular order. The example method can include additional steps as would be appreciated and understood by a person having pertinent skill in the art. The example method can be performed using an example assembly as disclosed herein, a variation thereof, or an alternative thereto as would be appreciated and understood by a person skilled in the pertinent art.

An assembly comprising a secondary valve accessory device and a catheter can be selected such that an elongated shaft of the catheter extends through a secondary seal of the secondary valve accessory and an end effector of the catheter is positioned within a tubular inner housing of the secondary valve accessory.

An outer housing of the secondary valve assembly can be attached to a proximal end of a sheath introducer such that the secondary valve is aligned with a primary valve of the sheath introducer and an intermediate chamber is bounded at least in part by the secondary seal, the primary seal, and the tubular inner housing The catheter shaft can be moved distally to thereby move the end effector of the catheter out of the tubular inner housing and through the primary seal.

These and other aspects of the disclosed technology are described herein along with the accompanying figures. Other aspects, features, and elements of the disclosed technology will become apparent to those skilled in the pertinent art upon reviewing the following description of specific examples of the disclosed technology. While features of the disclosed technology may be discussed relative to certain examples and figures, the disclosed technology can include one or more of the features or elements discussed herein. Further, while one or more examples may be discussed as having certain advantageous features, one or more of such features may also be used with the various other examples of the disclosure discussed herein. In similar fashion, while certain examples, implementations, and embodiments may be discussed below with respect to a given device, system, or method, it is to be understood that such examples can be implemented in various other devices, systems, and methods of the present disclosure.

DETAILED DESCRIPTION

Figure 1:
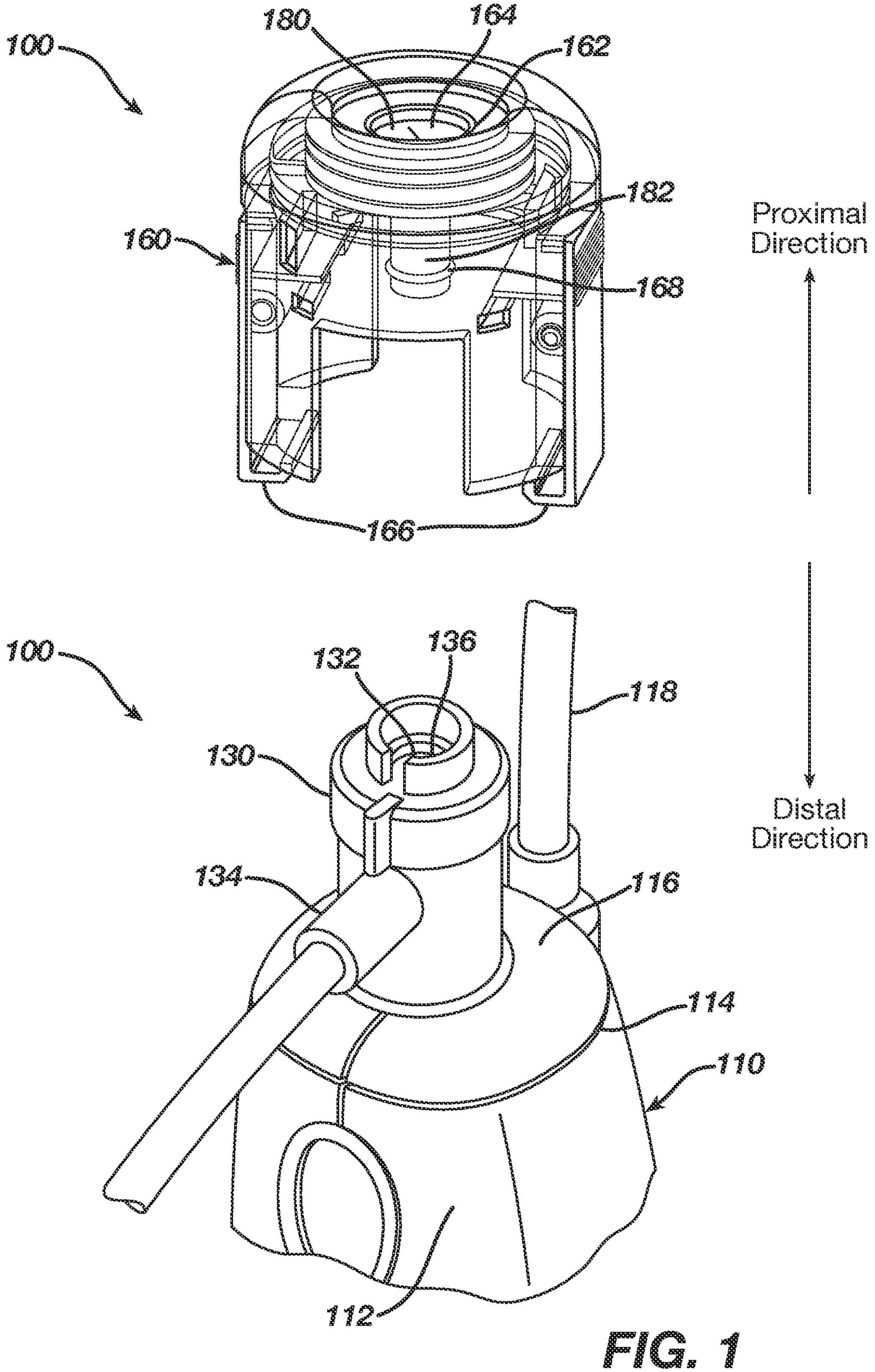
FIG. 1 illustrates an example sheath introducer assembly with a secondary valve accessory device detached from a sheath introducer according to aspects of the present invention.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g., "about 90%" may refer to the range of values from 71% to 99%.

As used herein, the terms "comprising" or "containing" or "including" are interpreted to mean that at least the named compound, element, particle, or method step is present in the composition or article or method, but does not exclude the presence of other compounds, materials, particles, method steps, even if the other such compounds, material, particles, method steps have the same function as what is named.

As used herein, the use of the term "external environment" is interpreted to mean an environment external to a medical device or assembly. When referring to the external environment of a medical device, assembly, or portion thereof that is external to a patient, the "external environment" is interpreted to be external to the patient. For instance, the "external environment" can include an environment in which a user interacts with the medical device/assembly.

As used herein, the use of terms such as "having," "has," "including," or "includes" are open-ended and are intended to have the same meaning as terms such as "comprising" or "comprises" and not preclude the presence of other structure, material, or acts. Similarly, though the use of terms such as "can" or "may" are intended to be open-ended and to reflect that structure, material, or acts are not necessary, the failure to use such terms is not intended to reflect that structure, material, or acts are essential. To the extent that structure, material, or acts are presently considered to be essential, they are identified as such.

As used herein, the terms "tubular" and "tube" are to be construed broadly and are not limited to a structure that is a right cylinder or strictly circumferential in cross-section or of a uniform cross-section throughout its length. For example, the tubular structure or system is generally illustrated as a substantially right cylindrical structure. However, the tubular system may have a tapered or curved outer surface without departing from the scope of the present invention.

Ranges described as being between a first value and a second value are inclusive of the first and second values, as well as all values therebetween. Likewise, ranges described as being from a first value and to a second value are inclusive of the first and second values, as well as all values therebetween.

It is also to be understood that the mention of one or more method steps does not preclude the presence of additional method steps or intervening method steps between those steps expressly identified.

The components described hereinafter as making up various elements of the disclosure are intended to be illustrative and not restrictive. Many suitable components that would perform the same or similar functions as the components described herein are intended to be embraced within the scope of the disclosure. Such other components not described herein can include, but are not limited to, for example, similar components that are developed after development of the presently disclosed subject matter.

In some examples presented herein, a secondary valve can be connected to the proximal end of a sheath introducer to work in conjunction with a primary valve of the sheath introducer, thereby resulting in a compound valve system. In some examples, the compound valve system can reduce air entrainment into the sheath introducer compared to a similar sheath introducer lacking the secondary valve because the secondary valve inhibits air from traveling through the compound valve system. Additionally, the compound valve system can be modified to dampen pressure buildups during catheter retraction by allowing internal volume expansion with pressure increase within the sheath introducer with compound valve.

The compound valve system can be integral to the sheath introducer or integral to a secondary valve accessory device that can be attached to a proximal end of the sheath introducer.

In some examples, the secondary valve can be designed to interface with a specific diameter of intralumenal device (e.g., specific catheter shaft diameter). In some such examples, the secondary valve opening can be sized large enough to allow a catheter shaft to pass therethrough but too small to allow a larger end effector to pass therethrough. In some such examples, the secondary valve can be integral to a secondary valve accessory device that can be built onto an end effector introducer tool so that the secondary valve accessory device is integral to the intralumenal device. Such examples can allow easy insertion of a large end effector of a catheter through a primary valve having a larger opening than the secondary valve opening. The smaller secondary valve opening can be effective to reduce risk of leak and air entrainment.

In some examples, the compound valve system can include an aspiration port to reduce pressure between the primary and secondary valves. The aspiration port can be aspirated to remove bubbles to reduce risk of air entrainment. Aspiration can be used in addition to, or as a replacement for internal volume expansion in the compound valve system.

Reference will now be made in detail to examples of the disclosed technology, such as those illustrated in the accompanying drawings. Wherever convenient, the same references numbers will be used throughout the drawings to refer to the same or like parts.

FIG. 1 illustrates an example sheath introducer assembly 100 including a secondary valve accessory device 160 and a sheath introducer 110. The secondary valve accessory device 160 is illustrated detached from the sheath introducer 110. The secondary valve accessory device 160 can be manufactured separately from the sheath introducer 110 and subsequently attached by a user (e.g., physician or other health care provider). As illustrated, the secondary valve accessory device 160 can include latch extensions 166 configured to snap onto a ridge 114 at a proximal end 116 of a handle 112 of the sheath introducer 110. Additionally, or alternatively, the secondary valve accessory device 160 and the sheath introducer 110 can be assembled together by other suitable mechanical attachment mechanism (e.g., interference fit, screw threads, double sided tape, adhesive, etc.) as understood by a person skilled in the pertinent art. Alternatively, a secondary hemostatic valve assembly 162 similar to that of the illustrated secondary valve accessory device 160 can be integral to the sheath introducer 110.

The sheath introducer 110 can be configured similarly to introducers known in the art. The sheath introducer 110 can be deflectable such as described in U.S. Pat. No. 10,046,141 incorporated herein by reference and attached in the Appendix of priority application U.S. 63/272,722, a CARTO VIZIGO® Bi-Directional Guiding sheath by Biosense Webster, and/or a MOBICATH® Sheath by Biosense Webster. Alternatively, the sheath introducer can be fixed similar to a CARDIAGUIDE™ Fixed Sheath by Biosense Webster. The sheath introducer 110 can have an identical structure to known sheath introducers, or a structure similar to known sheath introducers that is modified to include one or more mating features 114 such as, but not limited to, a ridge and/or threads to facilitate attachment.

The sheath introducer 110 can include a primary hemostatic valve assembly 130 having a primary valve opening 132. The primary valve opening can be sized to receive an intralumenal device 150 (see FIG. 2) to facilitate catheter based diagnostics and/or treatments (e.g., mapping, ablation, etc.). The sheath introducer 110 can include a side port 134 similar to some known sheath introducers. The sheath introducer 110 can include an electrical connector 118 similar to some known sheath introducers.

The secondary valve accessory device 160 can include a secondary valve opening 164 that aligns to the primary valve opening 132 of the sheath introducer 110 when the secondary valve accessory device 160 is attached to the sheath introducer 110. The secondary valve accessory device 160 can include an inner housing 182 having a funnel shape that can function as an introducer tool for an intralumenal device. The secondary valve accessory device 160 can include an O-ring 168 around an outside surface of the inner housing 182 that is positioned to seal to a proximal end of the primary valve assembly 130 to create an intermediate chamber between the primary seal 136 and the secondary seal 180.

Figure 2:
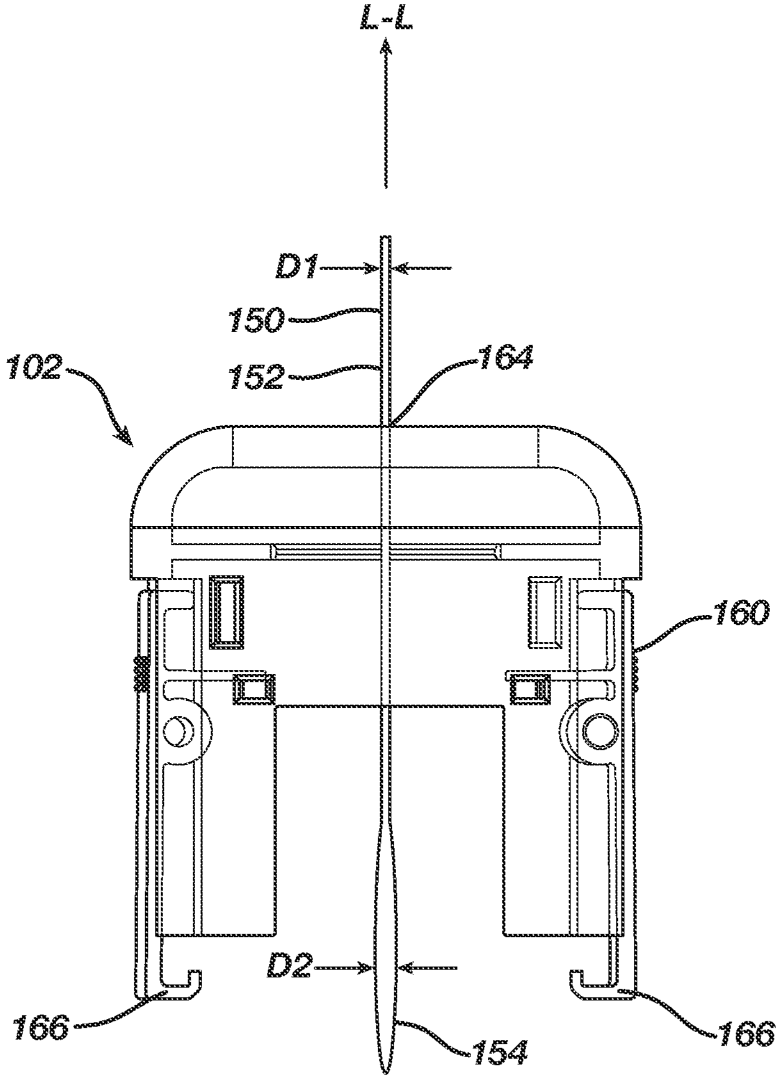
FIG. 2 illustrates an example catheter and secondary valve assembly including an intralumenal device and the secondary valve accessory device according to aspects of the present invention.

FIG. 2 illustrates an example intralumenal device and secondary valve assembly 102 including an intralumenal device 150 and the secondary valve accessory device 160. The intralumenal device 150 can include a catheter shaft 152 and an end effector 154. The intralumenal device 150 can be configured similar to any number of known devices including catheters for diagnostics and/or treatments. The end effector 154 can have a diameter D2 that is larger than a diameter D1 of the catheter shaft 152. For instance, the end effector 154 can include spine(s), lasso(s), balloon(s), and other such structures. The end effector 154 may be collapsed for delivery through the primary valve opening 132 of the sheath introducer 110 and can be configured to expand upon exiting a distal end of the sheath introducer 110.

For the sake of illustration, the end effector 154 is shown extending distally from the secondary valve accessory device 160. In practice, the end effector 154 can be positioned within the inner housing 182 (see FIG. 1) prior to attachment of the secondary valve accessory device 160 to the sheath introducer 110, and the inner housing 182 can function as an introducer tool that aids insertion of the end effector 154 through the primary valve opening 132 and into the sheath introducer 110. The intralumenal device and secondary valve assembly 102 can be pre-assembled for use by a user with the end effector 154 pre-loaded into the inner housing 182. To use the intralumenal device and secondary valve assembly 102 with the sheath introducer 110, the user may first attach the secondary valve accessory device 160 to the proximal end 116 of the sheath introducer 110, then push the catheter shaft 152 distally to move the end effector 154 distally from the inner housing 182 of the secondary valve accessory device 160, through the primary valve opening 132, and into an elongated shaft 120 of the sheath introducer (see FIGS. 3B and 3C).

When the intralumenal device and secondary valve assembly 102 is configured as such, the secondary valve opening 164 can be sized smaller than the primary valve opening 132 because the secondary valve opening 164 can be sized to receive the smaller diameter D1 of the catheter shaft 152 while the primary valve opening is sized to receive the larger diameter D2 of the end effector 154. The tighter seal of the secondary valve opening 164 around the catheter shaft 152 can therefore reduce risk of leak and air entrainment compared to a system in which all seal(s) must be sized to accommodate the larger diameter D2 of the end effector 154.

The secondary valve accessory device 160 can further be configured to detach from the sheath introducer 110 so that subsequent intralumenal devices can be inserted into the sheath introducer 110.

Figure 3A:
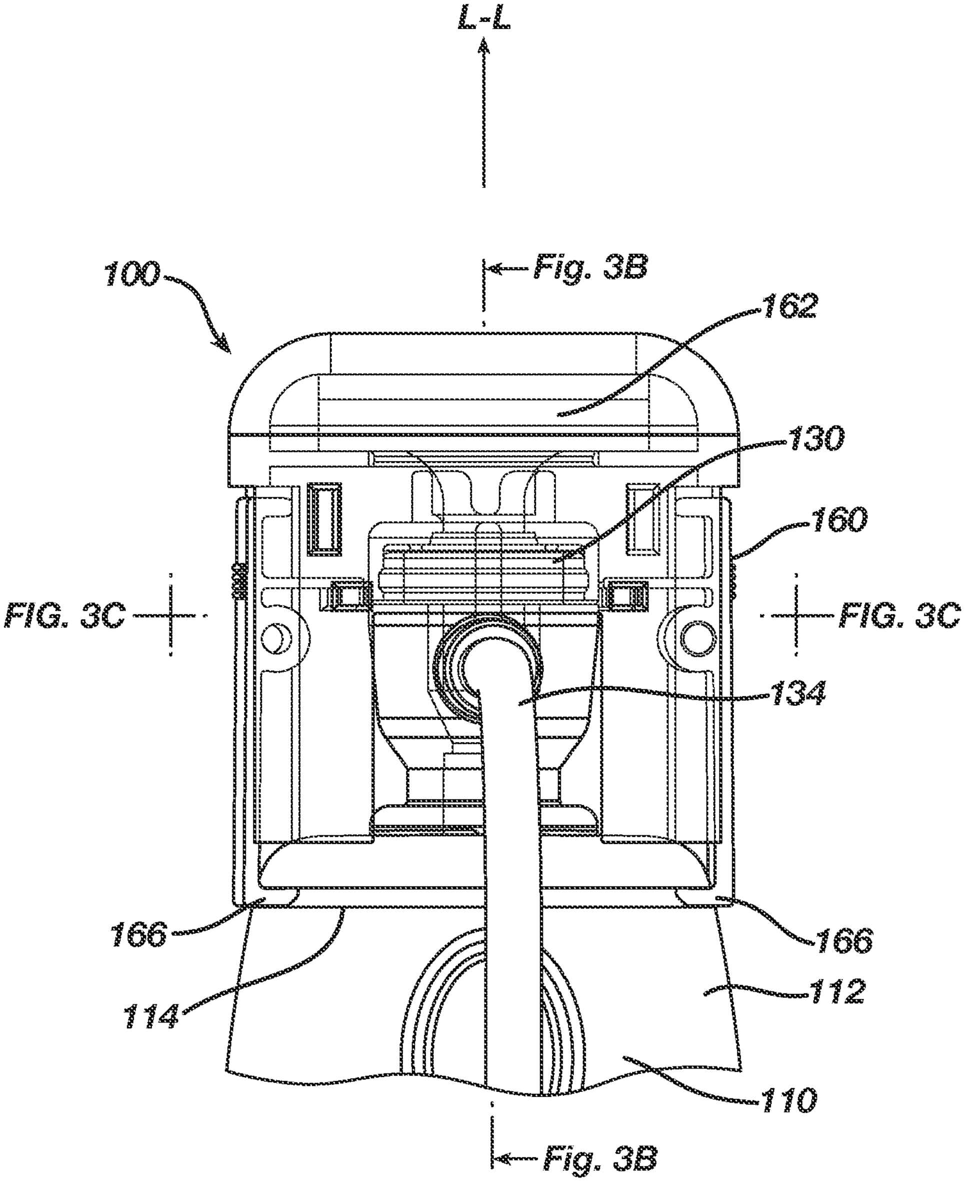
FIG. 3A illustrates a side view of a proximal end of the example sheath introducer assembly with the secondary accessory device attached to the sheath introducer according to aspects of the present invention.

FIG. 3A illustrates a side view of a proximal end of the example sheath introducer assembly 100 with the secondary accessory device 160 attached to the sheath introducer 110. The illustration shows the side port 134 rotated to the forefront.

Figure 3B:
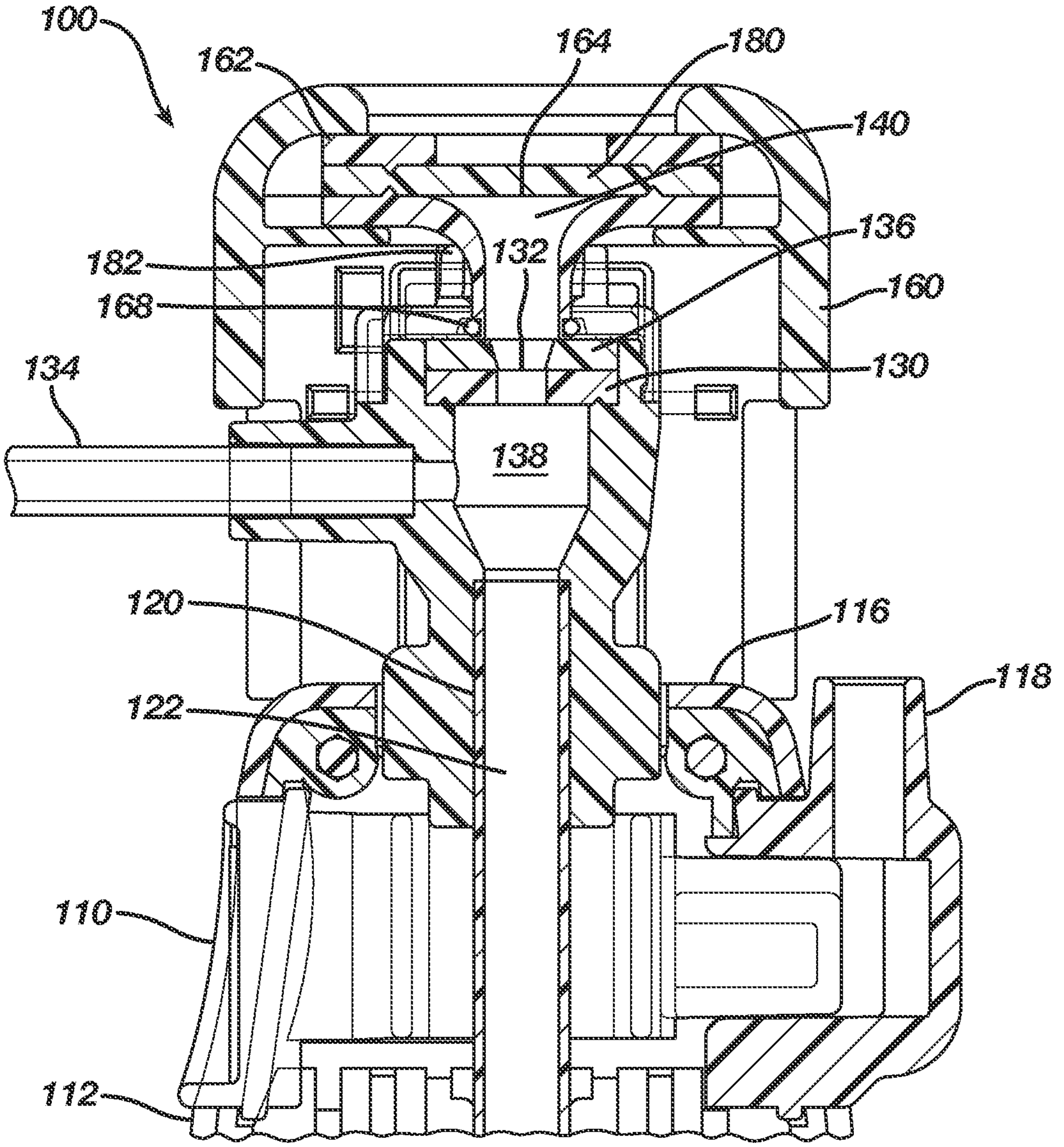
FIGS. 3B and 3C illustrate cross-sectional views of the example sheath introducer assembly as indicated in FIG. 3A according to aspects of the present invention.

FIG. 3B illustrates a cross-sectional view of the example sheath introducer assembly in a plane perpendicular to the plane of the page as indicated in FIG. 3A.

Figure 3C:
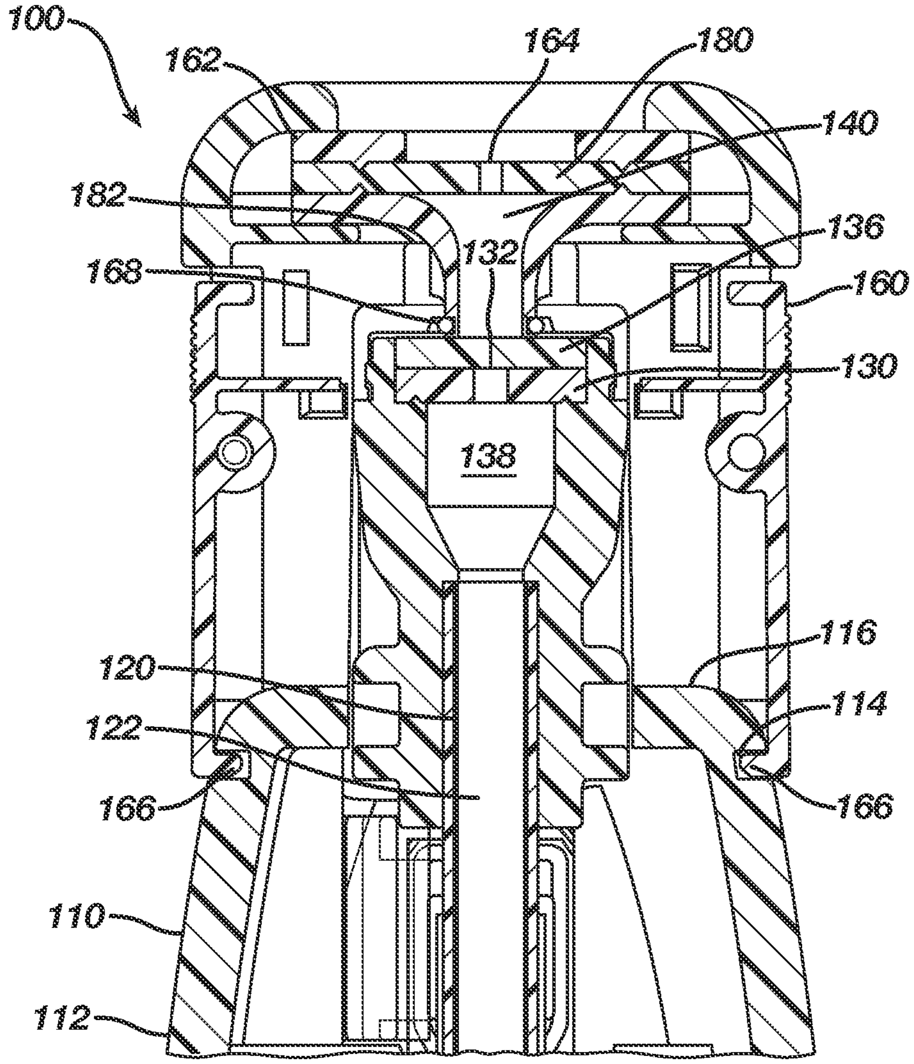

FIG. 3C illustrates a cross-sectional view of the example sheath introducer assembly in a plane parallel to the plane of the page as indicated in FIG. 3A.

Referring collectively to FIGS. 3B and 3C, the sheath introducer assembly 100 includes an intermediate chamber 140 between a secondary seal 180 of the secondary hemostatic valve assembly 162 and a primary seal 136 of the primary hemostatic valve assembly 130. The sheath introducer assembly 100 also includes a chamber 138 on the distal side of the primary seal 136 that leads distally to a lumen 122 of the elongated shaft 120 of the sheath introducer 110. The intermediate chamber 140 can be bound by the secondary seal 180, the primary seal 136, and the inner housing 182 of the secondary valve accessory device 160. The intermediate chamber 140 can be fluidically sealed, by the secondary seal 180 and the inner housing 182, from an external environment. The intermediate chamber 140 can be fluidically sealed, by the primary seal 136, from the chamber 138 on the distal side of the primary seal 136.

As illustrated in FIG. 3B, the side port 134 is in fluidic communication with the chamber 138 on the distal side of the primary seal 136, and thereby the side port 134 is in fluidic communication with the lumen 122 of the elongated shaft 120. Although not illustrated, the sheath introducer assembly 100 can further include a secondary side port in fluidic communication with the intermediate chamber 140. The secondary side port can be configured similarly to the side port 134 of the sheath introducer 110 to allow aspiration of the intermediate chamber 140. In some examples including the secondary side port, the side port 134 of the sheath introducer 110 can be optional. The secondary side port can be integral to the secondary valve accessory device 160.

Figure 4:
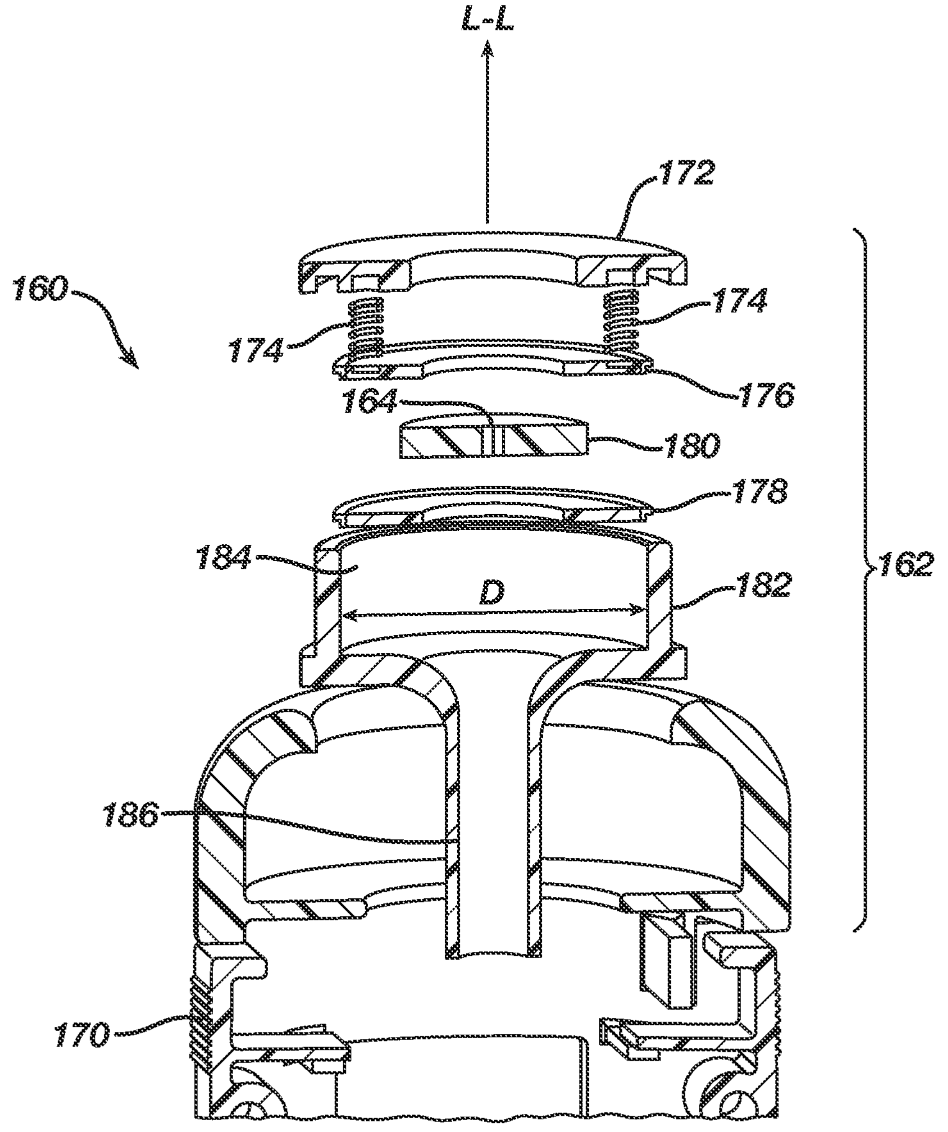
FIG. 4 illustrates an exploded view of an example secondary valve accessory device according to aspects of the present invention.

FIG. 4 illustrates an exploded view of the secondary valve accessory device 160 modified so that the secondary seal 180 is able to move in the direction of the longitudinal axis L-L ("longitudinally") in response to a pressure differential between the intermediate chamber and an external environment, wherein the secondary valve 180 is positioned between the intermediate chamber 140 and the external environment. FIGS. 3B and 3C illustrate a stationary secondary seal 180. The stationary secondary seal 180 is simpler to manufacture and may be sufficient to reduce leakage and/or entrainment in many treatment methods. The movable secondary seal 180 may provide additional pressure dampening in treatment methods which typically result in larger pressure differentials. The secondary valve accessory device 160 illustrated in FIGS. 4 through 6 can be used in place of the secondary valve accessory device 160 illustrated in FIGS. 3B and 3C.

Referring to FIG. 4, the secondary hemostatic valve assembly 162 can include a proximal retainer ring 172, one or more springs 174, a proximal washer 176, the secondary seal 180, a distal washer 178, and the inner housing 182. The inner housing 182 can include a seal chamber 184 and a tubular extension 186. The seal chamber 184 can have an inner diameter D. The tubular extension 186 can include a funnel taper at its proximal end that opens to the seal chamber 184. The funnel taper can be shaped to guide an intralumenal device toward the longitudinal axis L-L.

The secondary valve accessory device 160 can include a housing 170 providing structural support for the secondary hemostatic valve assembly 162. As in the previous illustrations, the housing 170 can be configured to attach to the sheath introducer 110. Alternatively, the housing 170 can be integral to the sheath introducer 110.

Figure 5:
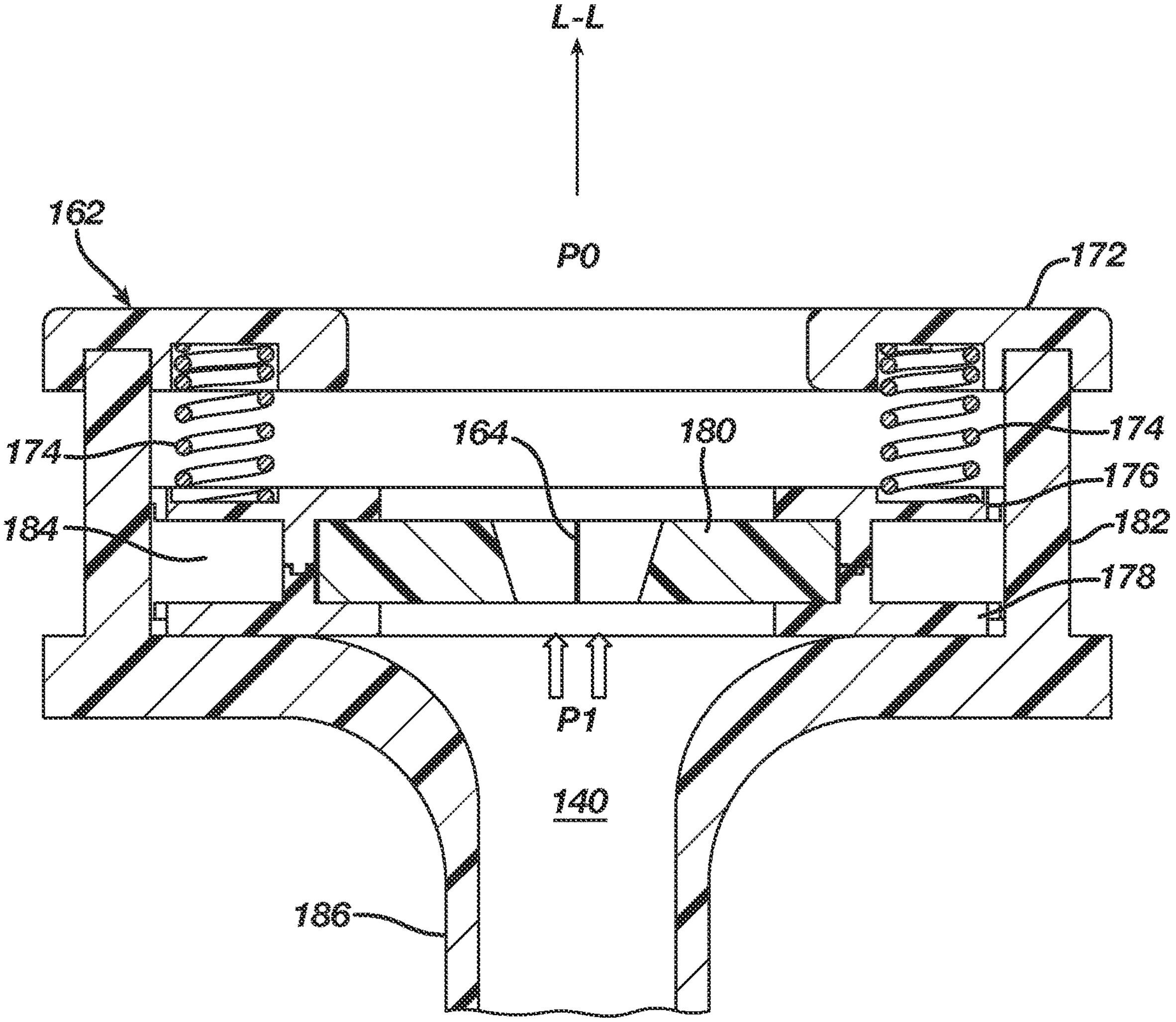
FIG. 5 illustrates a cross-sectional view of a secondary hemostatic valve assembly of the secondary valve accessory device in which a seal of the secondary hemostatic valve assembly is in a first position according to aspects of the present invention.

FIG. 5 illustrates a cross-sectional view of the secondary hemostatic valve assembly 162 of FIG. 4 in which the secondary seal 180 is in a first position. The secondary seal 180 is secured between the proximal washer 176 and the distal washer 178. The springs 174 extend between the proximal retainer ring 172 and the proximal washer 176 to press the distal washer 178 against a distal surface of the inner housing 182 within the seal chamber 184. The external environment is at an ambient pressure P0, and the intermediate chamber 140 is at an internal pressure P1. When the secondary seal 180 is in the first position, the pressure differential from the intermediate chamber to the external environment does not provide sufficient force on the secondary seal 180 to cause the springs 174 to compress.

Figure 6:
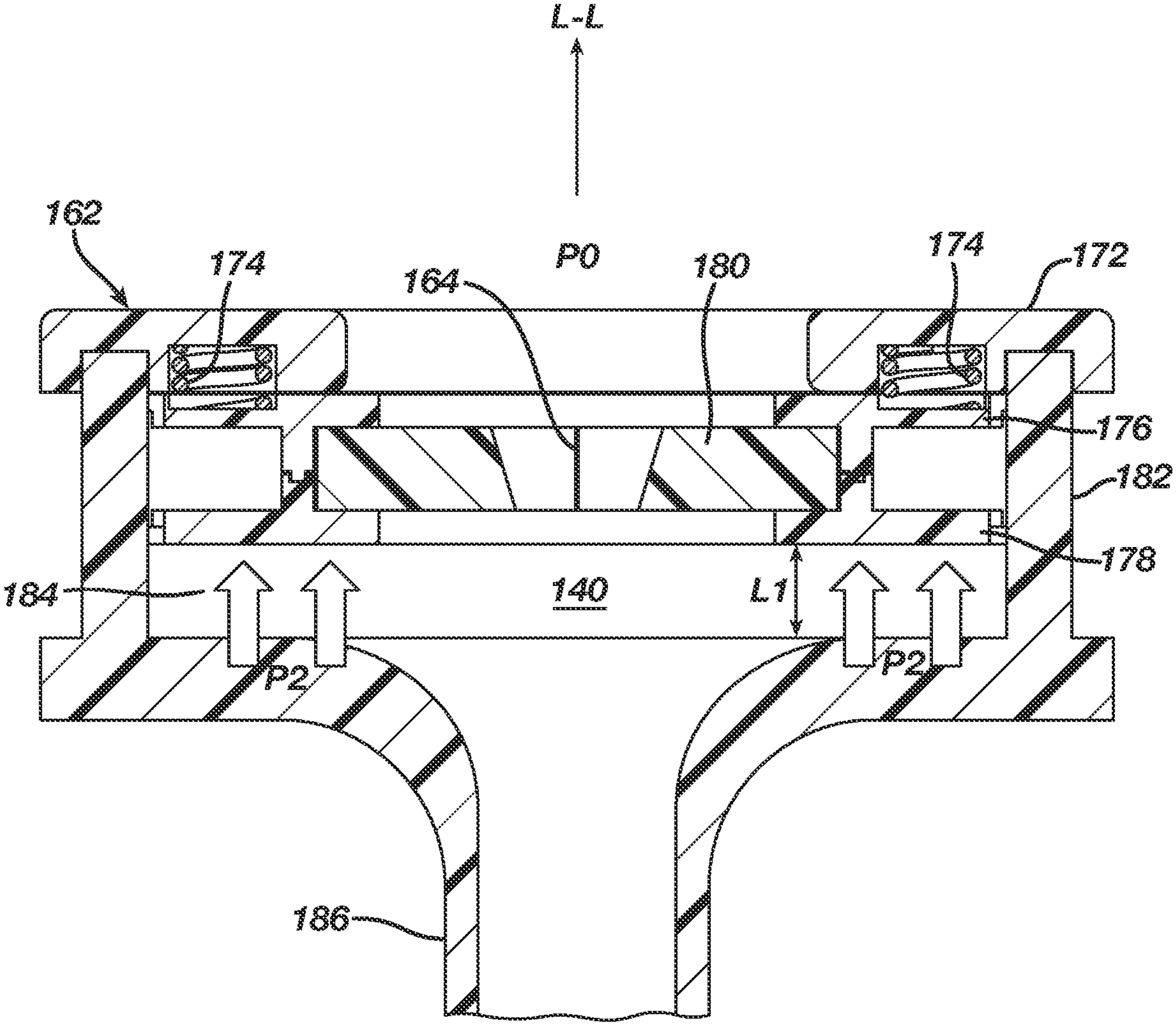
FIG. 6 illustrates a cross-sectional view of the secondary hemostatic valve assembly in which the seal of the secondary hemostatic valve assembly is in a second position according to aspects of the present invention.

FIG. 6 illustrates a cross-sectional view of the secondary hemostatic valve assembly 162 of FIG. 4 in which the secondary seal 180 is in a second position. The intermediate chamber 140 is at an increased pressure P2 such that the pressure differential from the intermediate chamber to the external environment provides sufficient force to cause the springs 174 to compress to their fullest extent. The spring force can be tailored to cause the secondary seal 180 to move from the first position to the second position, and a contiguous range of positions therebetween, as a function of pressure differential between the intermediate chamber 140 and the external environment as understood by a person skilled in the pertinent art.

The secondary seal 180 is translated a length L1 upon moving from the first position to the second position. The translation of the secondary seal 180 increases the internal volume of the intermediate chamber 140 by a volume that can be calculated as cross-sectional area of the seal chamber 184 times the translated length L1, where the change in internal volume can be equal to $pi\times(\frac{1}{2} D)^2\times L1$ for a cylindrical seal chamber 184. The increase in volume of the intermediate chamber 140 can be effective to decrease the pressure within the intermediate chamber, and thereby reduce risk of leakage through the secondary valve opening 164. The amount of pressure relieved is a function of increase in internal volume of the intermediate chamber 140 where the greater the change in volume, the greater the amount of pressure relieved.

Pressure damping is therefore determined by spring force and change in internal volume of the intermediate chamber 140. The spring stiffness and/or change in internal volume can be designed to damp a specific pressure profile related to manipulating of a specific intralumenal device through a specific sheath. For instance, an intralumenal device having a large balloon end effector may result in higher pressure differentials compared to a an intralumenal device having a smaller end effector or an end effector with spines when delivered through the same sheath introducer, and the same intralumenal device delivered through a smaller sheath introducer may result in higher pressure differentials compared to the same intralumenal device delivered through a larger sheath. The spring force and volume can be increased for higher pressure differentials and decreased for lower pressure differentials.

The chamber 138 on the distal side of the primary seal 136 (see FIGS. 3B and 3C) can be at a third pressure. The third pressure can be the same or different from the pressure of the intermediate chamber 140. In some examples, the primary valve opening 132 can be larger than a primary valve opening of a sheath introducer lacking the secondary hemostatic valve assembly 162 for comparable treatment methods because the secondary hemostatic valve can compensate for leakage and/or entrainment through the primary valve opening 132. In some examples, a larger primary valve opening 132 may be desirable to accommodate a large end effector. Therefore, some fluidic exchange between the intermediate chamber 140 and the chamber 138 on the distal side of the primary seal 136 can be tolerated, which can result in reduced pressure differential between the intermediate chamber 140 and the chamber 138 on the distal side of the primary seal 136.

Figure 7:
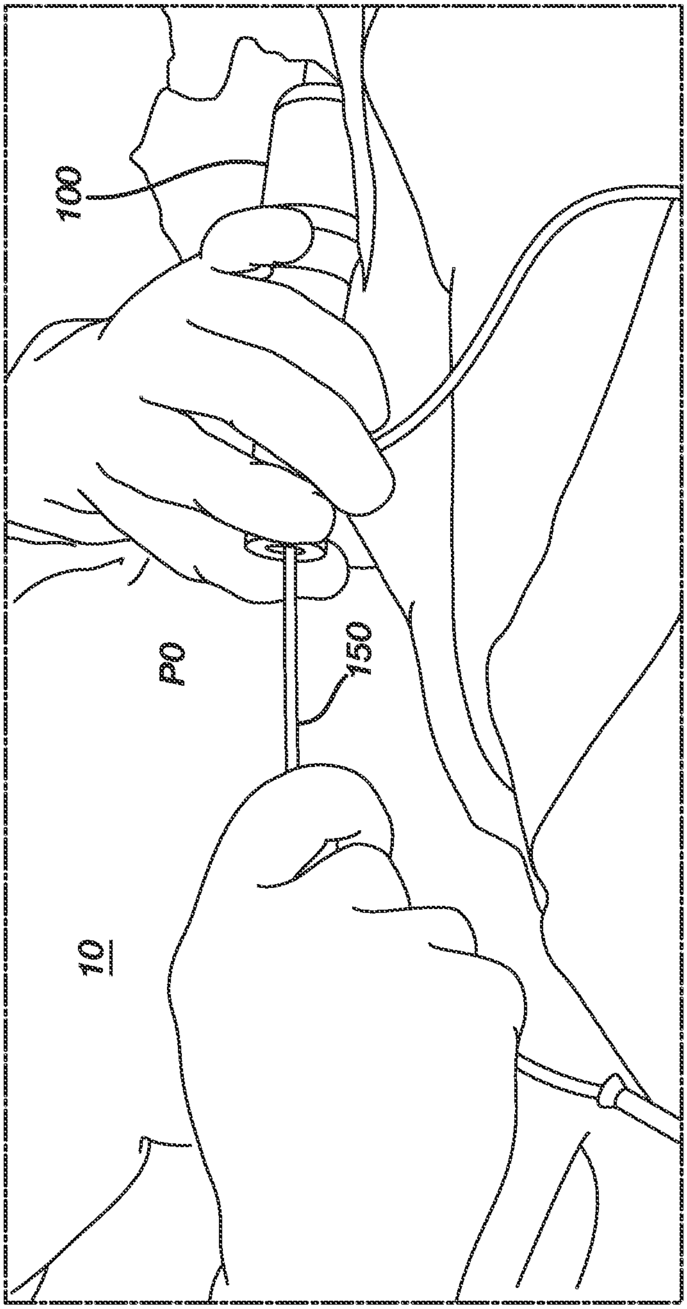
FIG. 7 illustrates a sheath introducer assembly in use according to aspects of the present invention.

FIG. 7 illustrates the sheath introducer assembly 100 and intralumenal device 150 in use. A user 10 is manipulating the intralumenal device 150 which is inserted through the compound valve assembly of the sheath introducer assembly 100. The user 10 is in an external environment at a pressure P0. When retracting the intralumenal device 150 from the sheath introducer assembly 100, the compound valve can reduce likelihood of outward leaks due to accumulation of pressure within the sheath introducer 110 compared to operation of a similar system lacking the secondary hemostatic valve assembly 162. In some treatments in which the intralumenal device has a large or uniquely shaped end effector, the compound valve can reduce likelihood of air entrainment when the end effector breaches the primary seal compared to operation of a similar system lacking the secondary hemostatic valve assembly 162. In some treatments, the compound valve can be effective to reduce leakage when pressure within the chamber 138 on the distal side of the primary seal 136 measures from about 10 to about 15 pounds per square inch (psi) when measured through the side port 134.

Figure 8A:
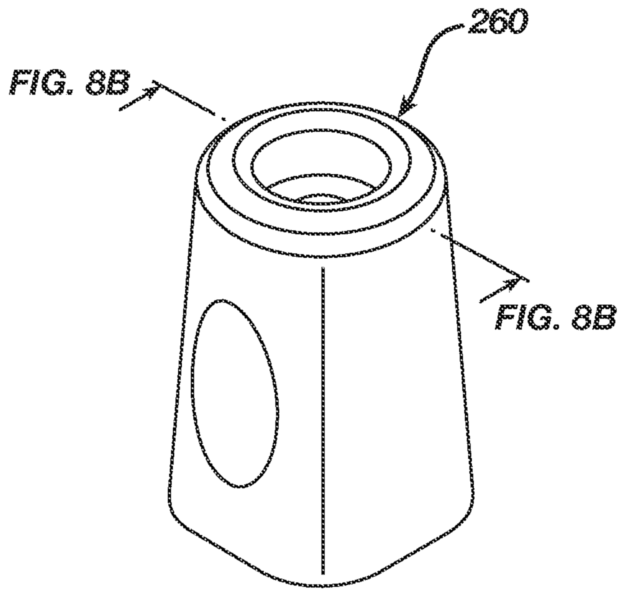
FIG. 8A illustrates another example secondary valve accessory device according to aspects of the present invention.

FIG. 8A illustrates another example secondary valve accessory device 260.

Figure 8B:
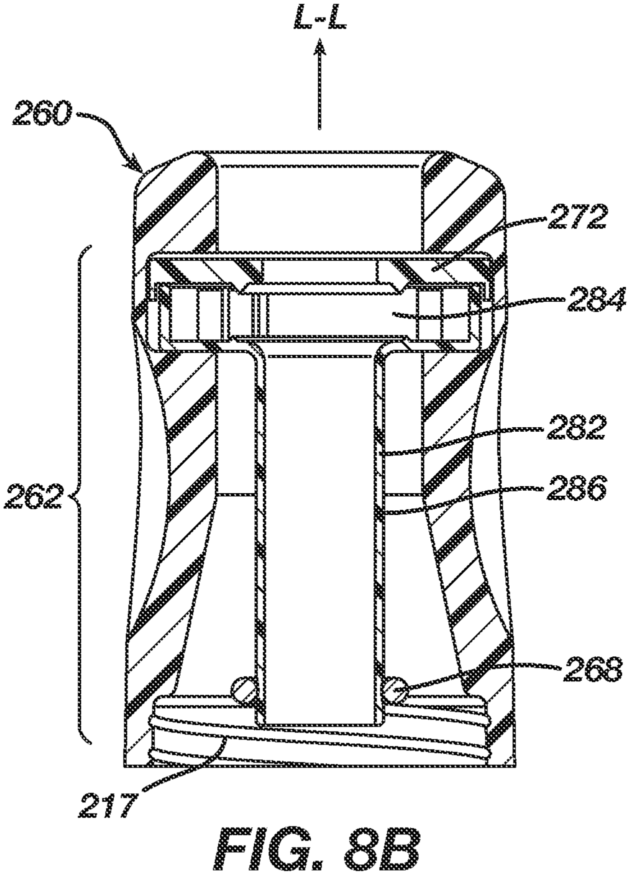
FIG. 8B illustrates a cross-sectional view of the secondary valve accessory device as indicated in FIG. 8A according to aspects of the present invention.

FIG. 8B illustrates a cross-sectional view of the secondary valve accessory device 260 as indicated in FIG. 8A. The secondary valve accessory device 260 illustrated in FIGS. 8A and 8B can be configured similarly to the secondary valve accessory device 160 illustrated in FIGS. 1 through 6. The secondary valve accessory device 260 illustrated in FIGS. 8A and 8B includes a housing 270 having threads 217 rather than latch extensions 166 as illustrated in FIGS. 1 through 3C. The secondary valve accessory device 260 illustrated in FIGS. 8A and 8B can therefore be screwed onto a sheath introducer configured similarly to the sheath introducer 110 illustrated in FIGS. 1 through 3C but for having screw threads in place of the ridge 114.

The secondary valve accessory device 260 illustrated in FIGS. 8A and 8B includes a secondary hemostatic valve assembly 262 including a proximal retainer ring 272, an inner housing 282, and an O-ring 268. The secondary valve assembly 260 can further include a stationary secondary seal similar to as illustrated in FIG. 3B, 3C or a movable secondary seal positioned within a seal chamber 284 of the inner housing 282 similar to as illustrated in FIGS. 4, 5, and 6. The inner housing 282 can further include a tubular extension 286. The length of the tubular extension 286 can be sized to fit an end effector of predetermined size so that the secondary valve accessory device 260 can be integrated with an intralumenal device similar to the intralumenal device and secondary valve assembly 102 illustrated in FIG. 2.

Figure 9:
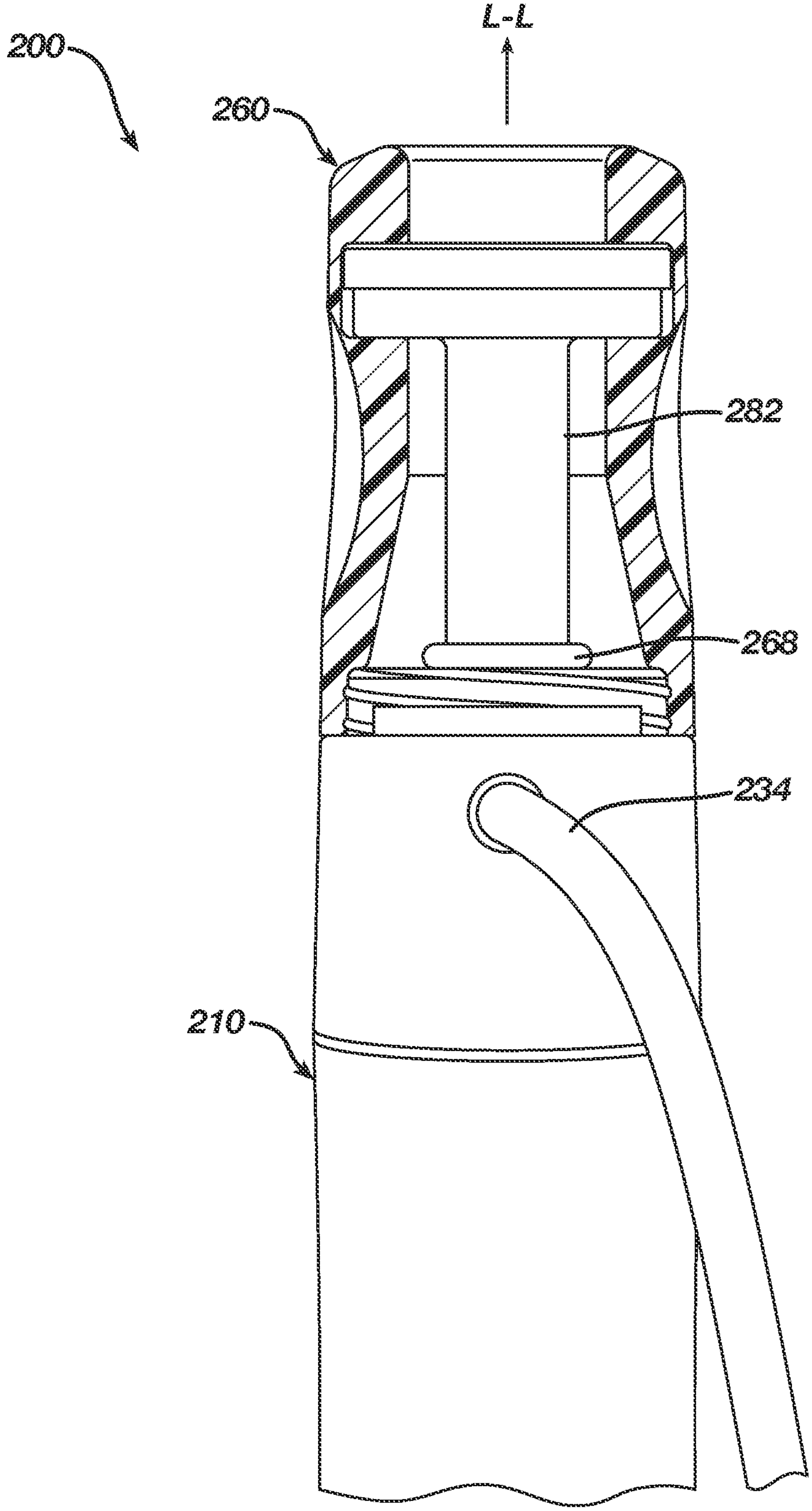
FIG. 9 illustrates a cut-away view of another example sheath introducer assembly including the secondary valve accessory device illustrated in FIGS. 8A and 8B according to aspects of the present invention.

FIG. 9 illustrates a cut-away view of an example sheath introducer assembly 200 including the secondary valve accessory 260 illustrated in FIGS. 8A and 8B and a sheath introducer 210 having a threaded proximal end and a side port 234. The sheath introducer assembly 200 can function and be configured similarly to the sheath introducer assembly 100 illustrated in FIGS. 1 through 7 and described elsewhere herein.

The descriptions contained herein are examples of embodiments of the invention and are not intended in any way to limit the scope of the invention. As described herein, the invention contemplates many variations and modifications of system components, including alternative combinations of components illustrated in separate figures, alternative materials, alternative component geometries, and alternative component placement. Modifications and variations apparent to those having skilled in the pertinent art according to the teachings of this disclosure are intended to be within the scope of the claims which follow.

What is claimed is:

1. A catheter sheath assembly, comprising:

an elongated shaft comprising a distal end, a proximal end, and a lumen extending along a longitudinal axis and providing a passageway into the proximal end of the shaft and out of the distal end of the shaft;

a primary hemostatic valve assembly fluidically sealing to the proximal end of the elongated shaft and comprising a primary seal; and a secondary hemostatic valve assembly comprising:

an inner housing;

a secondary seal disposed in a proximal direction in relation to the primary seal, the secondary seal engaged axially between a proximal washer and a distal washer, the secondary seal being configured to move relative to the primary seal parallel to the longitudinal axis by sliding of the proximal and distal washers along an inner surface of the inner housing to thereby change an internal volume of an intermediate chamber, and one or more springs configured to change in length to thereby move the secondary seal in relation to the primary seal, the change in the internal volume being based at least in part on stiffness of the one or more springs, the one or more springs being configured to compress to increase the internal volume of the intermediate chamber, the inner housing being fixed relative to the primary hemostatic valve assembly and to the primary seal such that the primary hemostatic valve assembly and the secondary hemostatic valve assembly define the intermediate chamber disposed at least in part between the primary seal and the secondary seal.

2. The catheter sheath assembly of claim 1, the change in the internal volume being equal to an interior cross-sectional area of the intermediate chamber orthogonal to the longitudinal axis multiplied by a change in longitudinal position of the secondary seal.

3. The catheter sheath assembly of claim 1, the secondary seal being configured to move in response to a pressure differential between the intermediate chamber and an external environment.

4. The catheter sheath assembly of claim 1, the internal volume of the intermediate chamber being configured to change in response to a difference in pressure between the intermediate chamber and an external environment.

5. The catheter sheath assembly of claim 1, the primary seal comprising a primary valve opening aligned to the longitudinal axis, and the secondary seal comprising a secondary valve opening aligned to the longitudinal axis.

6. The catheter sheath assembly of claim 5, the primary valve opening being expandable to a larger diameter than the secondary valve opening.

7. The catheter sheath assembly of claim 1, the intermediate chamber being fluidically sealed from an external environment by the secondary seal and being sealed from the lumen of the elongated shaft by the primary seal.

8. The catheter sheath assembly of claim 1, the intermediate chamber being shaped by a tubular housing portion extending between the secondary seal and the primary seal.

9. The catheter sheath assembly of claim 1, further comprising:

a handle joining the elongated shaft to the primary hemostatic valve assembly and configured to be manipulated to reshape the elongated shaft, the secondary hemostatic valve assembly being integral to the handle.

10. The catheter sheath assembly of claim 1, further comprising:

an aspiration port in fluidic communication with the intermediate chamber.

11. The catheter sheath assembly of claim 1, the inner housing comprising a funnel opening comprising a wide proximal end positioned in a distal direction from the secondary seal and a narrow distal end positioned in the proximal direction from the primary seal.

12. The catheter sheath assembly of claim 1, the secondary hemostatic valve assembly comprising an O-ring around an outside surface of the inner housing that is positioned to seal to a proximal end of the primary hemostatic valve assembly against the inner housing to seal the intermediate chamber.

* * * * *